United States Patent [19]

Trost et al.

[11] Patent Number: 5,705,746

[45] Date of Patent: Jan. 6, 1998

[54] METHOD OF DETERMINING THE TRACTION OF MOTOR VEHICLE WHEELS

[75] Inventors: Diane Trost; Jürgen Trost, both of Grafenburg; Markus Raab, Kirchardt, all of Germany

[73] Assignee: Daimler-Benz AG, Stuttgart, Germany

[21] Appl. No.: 805,359

[22] Filed: Feb. 24, 1997

[30] Foreign Application Priority Data

Mar. 2, 1996 [DE] Germany .................. 196 08 064.9

[51] Int. Cl.$^6$ ............................................. B60Q 1/00
[52] U.S. Cl. .................. 73/146; 73/8; 180/170; 180/171; 180/271; 340/438; 340/441; 364/423.098; 364/424.034; 364/426.01
[58] Field of Search .............. 73/7, 8, 146; 180/170, 180/171, 172, 271; 340/438, 441, 444; 364/423.098, 424.034, 424.055, 426.01, 426.015, 426.018, 426.025, 426.027

[56] References Cited

U.S. PATENT DOCUMENTS

| | | |
|---|---|---|
| 5,350,035 | 9/1994 | Bodier et al. .................. 180/271 |
| 5,424,714 | 6/1995 | Kin et al. ........................ 180/271 |
| 5,481,455 | 1/1996 | Iwata et al. ................. 364/426.018 |
| 5,502,433 | 3/1996 | Breuer et al. .................. 73/146 |
| 5,532,678 | 7/1996 | Kin et al. ....................... 340/444 |
| 5,557,552 | 9/1996 | Naito et al. ..................... 340/438 |
| 5,612,879 | 3/1997 | Makino ........................... 340/438 |
| 5,659,290 | 8/1997 | Haeri ............................. 340/441 |

*Primary Examiner*—George M. Dombroske
*Assistant Examiner*—Eric S. McCall
*Attorney, Agent, or Firm*—Klaus J. Bach

[57] ABSTRACT

In a method of determining the traction of motor vehicle wheels on wet pavements, a surge force generated by a water film on the pavement in front of at least one of the vehicle wheels is measured and from the measured surge force value and the instantaneous vehicle speed a critical speed at which the vehicle wheel will aqua-plane is determined and this critical speed is displayed to the driver or it is used to control a vehicle drive unit to keep the vehicle speed below the critical speed.

5 Claims, 2 Drawing Sheets

METHOD OF DETERMINING THE TRACTION OF MOTOR VEHICLE WHEELS

The invention relates to a method of determining the traction that is the ground adhesion of motor vehicle wheels on wet road surfaces wherein a force effective at least at one wheel is measured and from this measured force, a signal representative of the ground adhesion is generated.

DE OS 34 09 040 discloses a method wherein the loxodromic forces acting on a wheel rolling at an oblique angle are used as a measure for the instantaneous road surface traction of the wheel. Such forces are measured for example at wheels with toe-in adjustment. However, since the toe-in adjustment of vehicle wheels is only very small accurate termination of the loxodromic forces is not easily possible. This is especially true if the loxodromic forces are only very small so that they are hardly measurable at all. However, the smaller the loxodromic forces are the closer the wheel is at the critical point where ground adhesion is lost. Consequently, the moment at which a vehicle loses ground adhesion, for example because of aquaplaning, can not be determined accurately. As a result, a vehicle may have lost ground adhesion before a corresponding signal can be given to the driver.

DE OS 34 09 040 proposes to provide a fifth wheel specifically for measuring the loxodromic forces which is extended only when needed, the wheel being arranged so as to roll at an increased oblique angle so that it generates greater loxodromic forces. Such an additional retractable wheel however requires additional expenses and additional space. In addition, such a fifth wheel would have to be constantly extended when driving on wet roads if the driver wishes to be forewarned of possible ground adhesion loss. Such a wheel rolling at a relatively large oblique angle and used for extended periods increases the vehicle rolling resistance and, consequently, the fuel consumption and tire wear.

It is the object of the present invention to provide a method of determining the ground adhesion of vehicle wheels on wet road surfaces wherein a force effective at least at one of the vehicle wheels is permanently measured and from this force a signal representative of the wheel traction is generated.

SUMMARY OF THE INVENTION

In a method of determining the traction of motor vehicle wheels on wet road surfaces, a surge force generated by a road surface water film in front of at least one of the vehicle wheels is measured and from the measured surge force and the instantaneous vehicle speed a signal is generated corresponding to a critical speed at which the vehicle wheel will aquaplane and this speed signal is displayed to the driver or used to control a vehicle drive unit to keep the vehicle speed below the critical speed.

When driving on wet roads a water surge area is generated in front of the tires which has to be overcome by the vehicle wheels. This generates on the vehicle wheels a surge force which acts in the direction of the longitudinal vehicle axis and which increases with increasing vehicle speed. The surge force further increases with the thickness of the water film on the pavement. From this surge force effective on a wheel and the momentary vehicle speed a signal is generated in accordance with the invention which indicates the vehicle speed at which, with the instantaneous water film thickness, aqua planing of the vehicle could occur. Consequently, the driver can be reliably forewarned at which speed aqua planing may be expected. The vehicle speed can therefore be maintained at a level below the speed at which the vehicle wheels might lose traction. It is further possible in accordance with the invention to use the signal not exclusively for the information of the driver but to employ it as a control signal for the vehicle drive unit, for example for the power output control device of an internal combustion engine so as to reduce the vehicle speed automatically in order to prevent aquaplaning. Since the surge forces act in the direction of the longitudinal vehicle axis, there is no need for a fifth wheel rolling at an oblique angle to the driving direction.

The invention will be described below in greater detail on the basis of particular embodiment shown in the accompanying drawings.

DETAILED DESCRIPTION OF AN EMBODIMENT

Figure 1:
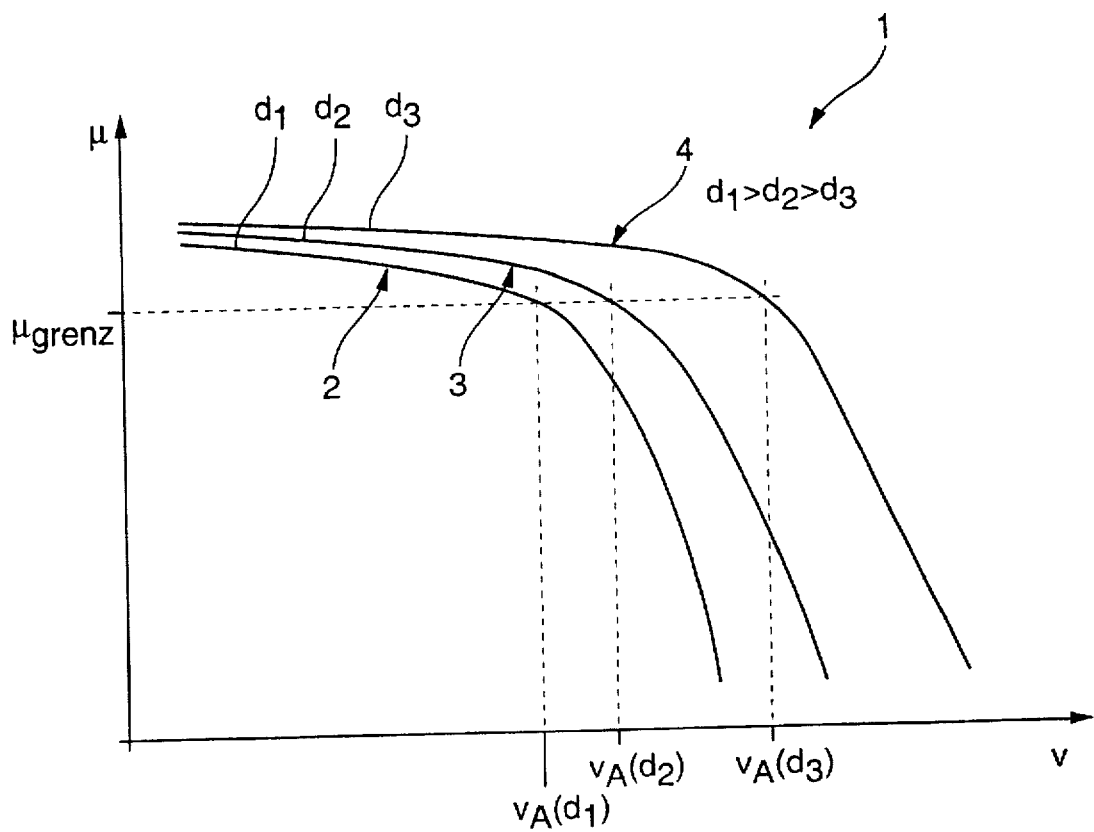
FIG. 1 shows in a diagram $\mu=f(u)$ the relationship between the friction between the wheel and the pavement.

FIG. 1 shows diagrammatically the functional relationship between the friction coefficient $\mu$ effective between the wheel of a motor vehicle on a wet pavement and the vehicle speed depending on the water film thickness d. For clearer representation, only three curves 2, 3, and 4 are shown wherein the curve 4 is for a relatively small water film thickness $d_3$, the curve 3 is for a medium water film thickness $d_2$, and the curve 2 is for a relatively large water film thickness $d_1$. It can be seen that, at low vehicle speeds, the curves are all relatively flat, that is, an increase in the vehicle speed causes only a relatively small reduction of the friction coefficient $\mu$ between the tires and the pavement. At speeds greater than certain limit values $v(d_1)$, $v(d_2)$, $v(d_3)$ respectively, the curves 2, 3 and 4 drop rapidly with small speed increases. The curve section which steeply declines with increasing vehicle speed indicates the speed range in which the wheel 5 that is its tire no longer rolls in direct contact with the pavement but on a water film forming between the tire and the pavement. In the areas of transition of the curves 2, 3, and 4 from the relatively flat sections to the steeply declining sections that is at a limit friction coefficient value $\mu_{grenz}$ aquaplaning of the wheel 5 starts. In other words the wheel 5 starts floating on the water film at the speeds V at which the respective curves have the transition areas between their relatively flat sections and the steeply inclined sections. This transition area or transition point $\mu_{grenz}$ moves with decreasing water film thickness d in the direction of higher vehicle speeds. Consequently, with $d_1 > d_2 > d_3$, the limit speed at which a wheel starts aquaplaning—which will be called from here on, the "planing speed" $V_A$—is the highest for the curve 4 with the smallest water film thickness $d_3$ and the lowest for the curve 2 with greatest water film thickness $d_1 (V_A(d_1) < V_A(d_2) < V_A(d_3))$.

Figure 2:
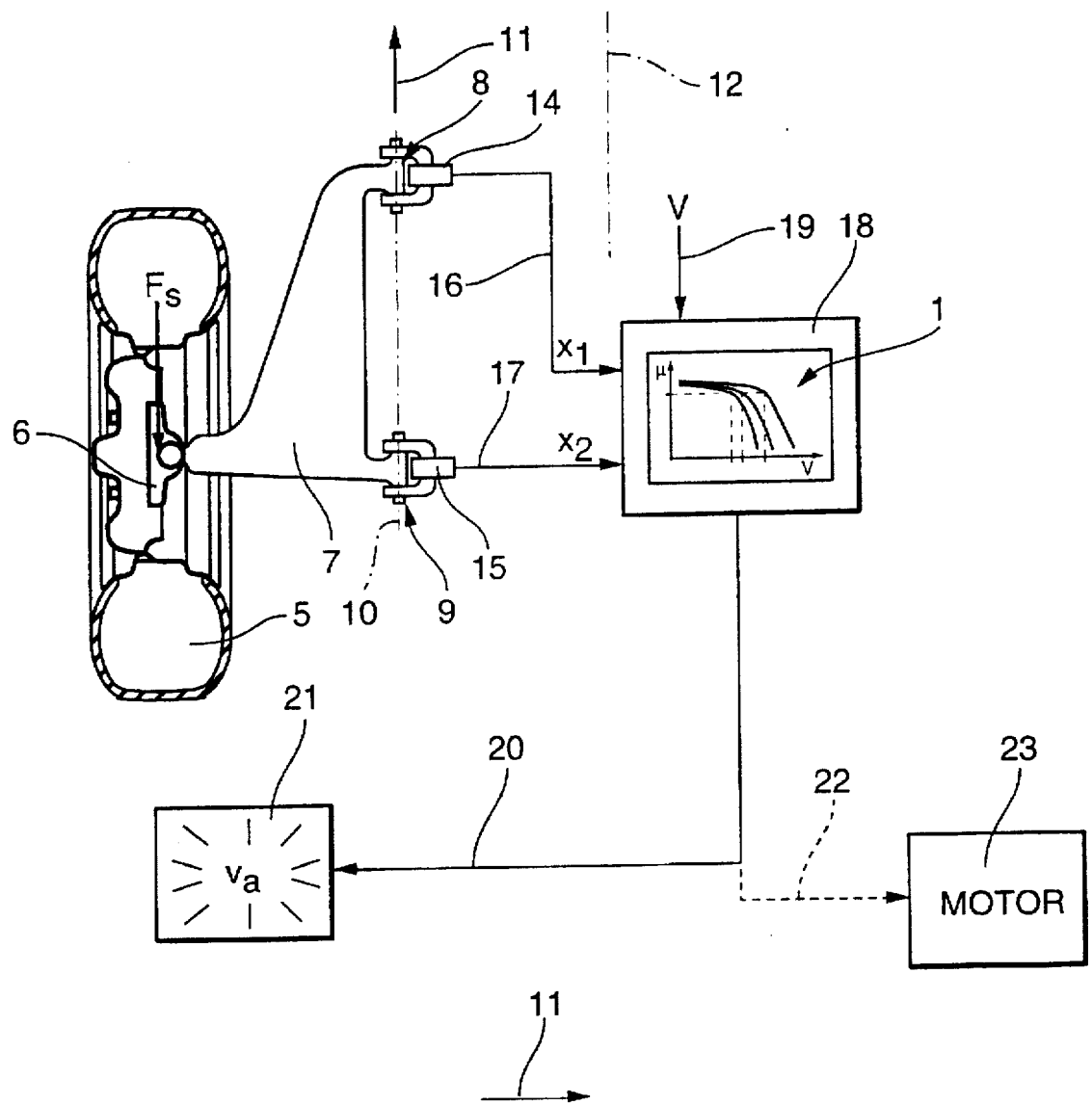
FIG. 2 shows, in principle, an arrangement for performing the method according to the invention.
Figure 3:
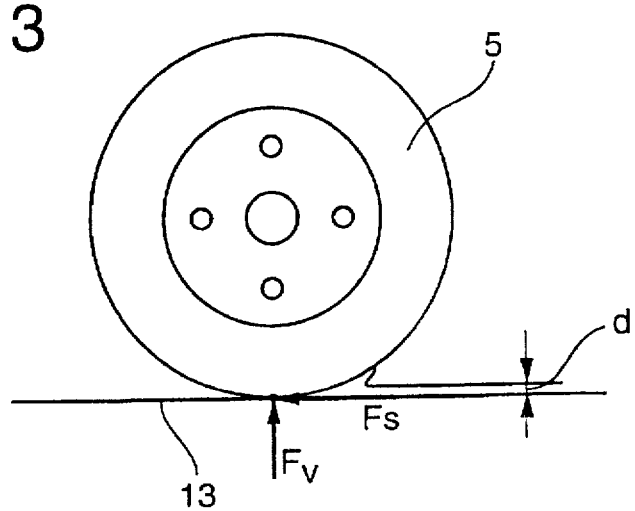
FIG. 3 is a side view of the wheel shown in FIG. 2 indicating the forces acting on the wheel.

FIG. 2 shows in a top view a motor vehicle front wheel 5, which is rotatably supported on a wheel carrier 6 and is linked, with a control arm 7, by means of elastic bearings 8 and 9 to a vehicle body which is not shown in the drawings. The wheel 5 is supported so as to pivot during spring action about a pivot axis 10 defined by the two bearing 8 and 9. If the wheel 5 rolls on wet pavement in the direction of the arrow 11, the wheel is subjected to a force effective in the direction of the longitudinal vehicle axis which force is called a surge force $F_s$ which increases with the vehicle speed V and with the water film thickness d. With the surge force $F_s$, the wheel 5 is further subjected to a vertical force $F_v$ effective on the wheel 5 in a direction normal to the road surface 13. The vertical force $F_v$ tends to lift the wheel 5 off the road surface 13 (see FIG. 3). The larger the vertical force component $F_v$ is, the smaller are the wheel adhesion to the pavement and the friction coefficient. The surge force $F_s$ corresponds to the vertical force component $F_v$, that is the larger the surge force $F_s$ is the larger is also the vertical force component $F_v$.

The surge force $F_s$ effective in the longitudinal direction is transmitted, by way of the control arm 7, to the elastic bearings 8 and 9 and causes a deformation of these bearings. This deformation is measured by means of sensors 14 and 15 arranged at the bearings 8 and 9 and the measured values are transmitted as deformation distances $x_1$ and $x_2$ in the form of electrical signals to an electronic control unit 18. The electronic control unit 18 further receives a signal indicating the actual vehicle speed value (arrow 19). On the basis of the instantaneous water film thickness d is determined (see also FIG. 3).

Depending on the instantaneous water film thickness d the planing speed $V_A$ is read from the respective curve in the diagram 1µ=f(v) (see FIGS. 1 and 2) and is transmitted to the driver by way of a control line 20 and a display 21 arranged in the vehicle cabin. The functional relationships between surge force $F_s$, vehicle speed V and water film thickness d as well as the functional relationships between the friction coefficient µ and the vehicle speed V (FIG. 1) are experimentally determined and stored in the memory of the control unit 18 as characteristic graphs.

With the method according to the invention, the driver can therefore obtain the information at which speed he may expect a loss of wheel traction by aqua planing long before the vehicle reaches the planing speed $V_A$. The loss of wheel adhesion by aqua planing can therefore be safely avoided by the driver by taking appropriate measures.

In another embodiment according to the invention, the control signal generated by the electronic control unit 18 is transmitted, by way of a control line 22 (shown by dashed lines) to a drive unit 23 (for example, an internal combustion engine) of the motor vehicle. The arrangement may be such that the power output control device of this drive unit 23 reduces the power output when a predetermined vehicle speed $V_2=V_A-\Delta V$ below the planing speed $V_A$ is reached.

Instead of using the distance sensors 14, 15 for determining the surge force $F_s$, two sensors may be utilized which sense the acceleration of the wheel carrier 6. One of the two sensors senses the acceleration in the longitudinal direction of the vehicle, and the other senses the acceleration of the wheel carrier in vertical direction.

It is of course not necessary to limit the determination of the surge force to one wheel. It could be determined just as well for two wheels, for example, the two front wheels of a vehicle. Then the planing speeds for the two front wheels could be compared and the planing speed VA of the wheel in greater danger of losing traction could be utilized for transmission to the display 21 or for the control of the drive unit 23.

What is claimed is:

1. A method of determining traction of motor vehicle wheels on a wet road surface, on which a surge force is generated by a water film on the road surface when said motor vehicle is rolling over said road surface in the longitudinal direction of said motor vehicle, comprising the steps of: measuring said surge force at least on one wheel of said motor vehicle, and generating from the measured surge force value and the instantaneous motor vehicle speed a signal corresponding to a critical speed at which, with a instantaneous water film thickness, the motor vehicle will plane (aqua planing speed).

2. A method according to claim 1, wherein said critical speed at which said motor vehicle will aqua-plane is indicated to the driver.

3. A method according to claim 1, wherein said critical speed at which said motor vehicle will aqua-plane is taken from a characteristic performance graph which has been determined experimentally.

4. A method according to claim 1, wherein said surge force is determined by at least one sensor sensing deformations in a motor vehicle wheel support structure.

5. A method according to claim 1, wherein said instantaneous vehicle speed signal and at least one other signal are supplied to an electronic control unit, said at least one other control signal being generated by sensors arranged at the jointure of a wheel control arm to a vehicle body so as to sense relative movement between said control arm and said vehicle body, and wherein said control unit generates a signal corresponding to an actual planing speed which signal is supplied to a display device arranged in the motor vehicle in view of the driver.

* * * * *